US006479989B2

(12) United States Patent
Taylor

(10) Patent No.: US 6,479,989 B2
(45) Date of Patent: *Nov. 12, 2002

(54) EDDY CURRENT PROBE WITH AN ADJUSTABLE BISECTED SENSING END

(76) Inventor: Albert Rudolph Taylor, 3245 Seymour Ave., Bronx, NY (US) 10469

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/416,868

(22) Filed: Oct. 13, 1999

(65) Prior Publication Data

US 2002/0027436 A1 Mar. 7, 2002

(51) Int. Cl.[7] .............................................. G01N 27/90
(52) U.S. Cl. ..................... 324/219; 324/233; 324/232; 336/84 M; 73/866.5
(58) Field of Search ................. 324/233, 219, 324/238, 220, 234, 232, 228, 262, 757, 758; 73/866.5; 336/84 M

(56) References Cited

U.S. PATENT DOCUMENTS

| | | | | |
|---|---|---|---|---|
| 3,340,466 A | * | 9/1967 | Ono .......................... 324/219 |
| 3,825,822 A | | 7/1974 | Förster ....................... 324/219 |
| 3,986,104 A | | 10/1976 | Randolph, Jr. ............... 324/232 |
| 4,016,487 A | | 4/1977 | Neumaier .................... 324/232 |
| 4,146,837 A | * | 3/1979 | Bashkirov ................... 324/225 |
| 4,237,419 A | | 12/1980 | Törnblom et al. ............ 324/225 |
| 4,286,216 A | | 8/1981 | Auld et al. .................. 324/237 |
| 4,414,508 A | | 11/1983 | Davis et al. ................. 324/238 |
| 4,467,281 A | | 8/1984 | Davis et al. ................. 324/232 |
| 4,495,466 A | | 1/1985 | Lakin ......................... 324/242 |
| 4,609,870 A | | 9/1986 | Lale et al. ................... 324/225 |
| 4,629,984 A | | 12/1986 | Scalese ....................... 324/228 |
| 4,646,013 A | * | 2/1987 | Tornblom .................... 324/225 |
| 4,652,822 A | | 3/1987 | Wallace ...................... 324/232 |
| 4,703,265 A | | 10/1987 | Törnblom .................... 324/232 |
| 5,006,800 A | | 4/1991 | Hedengren et al. .......... 324/233 |
| 5,138,269 A | * | 8/1992 | Deutsch ...................... 324/715 |
| 5,172,055 A | | 12/1992 | Horn ....................... 324/207.16 |
| 5,182,513 A | | 1/1993 | Young et al. ................ 324/232 |
| 5,237,271 A | | 8/1993 | Hedengren .................. 324/232 |
| 5,339,031 A | | 8/1994 | Chern ......................... 324/219 |
| 5,363,040 A | | 11/1994 | Horn .......................... 324/238 |
| 5,399,968 A | | 3/1995 | Sheppard et al. ............ 324/242 |
| 5,418,459 A | | 5/1995 | You et al. ................... 324/240 |
| 5,424,639 A | | 6/1995 | Meiffren et al. ............. 324/219 |
| 5,430,376 A | | 7/1995 | Viertl ......................... 324/227 |
| 5,446,378 A | | 8/1995 | Reich et al. ................. 324/238 |
| 5,574,368 A | | 11/1996 | Horn et al. .................. 324/228 |
| 5,600,240 A | | 2/1997 | Mikhailovich et al. ...... 324/219 |
| 5,610,517 A | * | 3/1997 | Ma et al. .................... 324/233 |
| 5,642,050 A | | 6/1997 | Shoemaker ................. 324/329 |
| 5,834,937 A | * | 11/1998 | Burris ......................... 324/219 |

* cited by examiner

Primary Examiner—Jay Patidar
(74) Attorney, Agent, or Firm—Bruce B. Brunda; Stetina Brunda Garred & Brucker

(57) ABSTRACT

In accordance with the present invention there is provided an eddy current probe for the detection of defects within a structure. The probe has a sensing end with a coil disposed therein. The coil is operative to generate an eddy current field within the structure when placed adjacent to the structure. Furthermore, the probe of the present invention includes a metallic shield disposed around the coil and operative to focus the eddy current field within the structure. In order to generate the eddy current field, the coil is in electrical communication with a frequency generator. The frequency generator is operative to generate a high and low frequency signal within the coil in order to enhance detection of defects within the structure.

9 Claims, 1 Drawing Sheet

EDDY CURRENT PROBE WITH AN ADJUSTABLE BISECTED SENSING END

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention generally relates to non-destructive inspection technology and more particularly to a device that utilizes eddy currents to detect cracks, flaws and other defects in materials.

Various instruments for flaw detection in structures have been developed that rely upon the generation of eddy currents in the body of the structure being tested. Flaws in the metallic structures are detected by their perturbation of the eddy currents. The eddy currents are generated in the metallic structure by positioning the structure within an alternating magnetic field. Perturbation of the eddy currents because of a localized presence of a defect in the metallic structure creates a resultant change in the magnetic flux associated with these eddy currents. When such change is detected, it is an indication of the presence of defects in the structure. Such use of eddy currents has been practiced for detecting flaws in solid metallic slabs, metallic pipes, and in layered metallic structures such as the outside surfaces of aircraft.

A single coil may be utilized in the eddy current test probe. The single coil induces a magnetic field in the structure being tested. Flaws are detected by noting changes in the voltage and phase angle of the signal applied to the test coil. Alternatively, a drive coil and a sense coil may be used for the eddy current test probe. Detection of flaws in the test structure is achieved by utilizing voltage variations in the sense coil. Typically, the voltage variations are detected utilizing a null bridge.

Detection of flaws utilizing eddy currents is accomplished by comparing the phase/voltage variations of the test coil to a known response for a particular defect.

Accordingly, the phase/voltage response of the test coil can be compared to a table of responses to determine the size and nature of the defect. The table of responses is generated by testing known defects with the eddy current test probe and detecting the phase/voltage response for such known defect.

Often times an inspection effort is difficult to accomplish due to the geometry, manufacture, service, interference, re-work and occasional abuse of the area. Any one of these factors or a combination thereof may require reaming and/or flex-honing of the inspection area to make such suitable. Additionally, false defect indications are sometimes encountered when metal chips are embedded between layers of stacked structures that form the structure. These chips must be removed mechanically before an accurate inspection effort can be undertaken. Accordingly, there is currently a need for an eddy current inspection probe which can accurately detect defects within structures in varying conditions.

Prior art eddy current probes do not provide consistent responses for defects smaller than 0.030". The depth-length aspect ratio for such cracks creates uncertainty of the phase/voltage response with conventional eddy current probes. The coils of prior art eddy current probes can typically detect small and large defects in a single frequency of the eddy current field. However, the magnetic field induced within the test structure is broad and less intense at the extremities of the defect such that the phase/voltage responses for the extremities of the defect vary greatly. Additionally, phase/voltage responses for such defects may vary over a range of frequencies applied to the coil of the eddy current probe.

The present invention addresses the above-mentioned deficiencies in prior art eddy current probes by providing a probe that is accurate over a broad range of frequencies. Accordingly, phase/voltage responses obtained for multiple frequencies generated by the eddy current probe can be compared to achieve greater accuracy of defect measurement. Additionally, the present invention provides for a focused eddy current measurement method such that an enhanced crack profile aspect ratio of the defect can be determined.

BRIEF SUMMARY OF THE INVENTION

In accordance with the present invention there is provided an eddy current probe for the detection of defects within a structure. The probe has a sensing end with a coil disposed therein. The coil is operative to generate an eddy current field within the structure when placed adjacent to the structure. Furthermore, the probe of the present invention includes a metallic shield disposed around the coil and operative to focus the eddy current field within the structure. In order to generate the eddy current field, the coil is in electrical communication with a frequency generator. The frequency generator is operative to generate a high and low frequency signal within the coil in order to enhance detection of defects within the structure.

In accordance with the present invention, the shield may be fabricated from a Mu metallic material that is ferromagnetic. The frequency generator typically produces a high frequency signal of approximately 1 MHz and a low frequency signal of approximately 150 KHz. In electrical communication with the coil is a voltage and phase sensor operative to determine the voltage and phase angle of the high and low frequency signals. The frequency and phase responses are indicative of the size of the defect in the structure such that an engineering analysis of the defect can be made. The high frequency signal determines the length of the defect whereas the low frequency signal determines the depth of the defect.

In the preferred embodiment of the present invention, the coil has a generally circular configuration and the shield is generally cylindrical. As such, the shield surrounds coil and focuses the direction of the eddy current field. The sensing end of the probe includes a slit in order to vary the diameter of the probe such that the probe may be insertable within a hollow structure. Typically, the sensing end includes a longitudinal axis and the coil is in generally spaced parallel relation to such axis. The sensing end may be generally spherical and attached to a generally cylindrical shaft in order to insert the probe within the interior of the structure to be analyzed.

In accordance with the preferred embodiment of the present invention, there is provided a method of determining a size of a defect within a hollow structure using an eddy current probe having a coil shielded by a Mu metallic material. The method comprises the steps of inserting the probe within the interior of the structure and generating a high and low frequency signal within the coil. Accordingly, an eddy field is produced within the structure and focused by the Mu shield. The phase angle and voltage response of the high and low frequency signals are detected to determine the size of the defect.

The high and low frequency signals are generated by a frequency generator and applied to the coil simultaneously and analyzed separately in order to determine the size of the defect. In order to fully analyze the defect, the probe is rotated within the hollow interior of the structure in order to scan the entire inside surface thereof. A voltage and phase angle analyzer detects the voltage and phase angle of the high and low frequencies in order to determine a size of the defect. Typically the high frequency signal is analyzed to determine the length of the defect and the low frequency signal is analyzed to determine the depth of the defect.

BRIEF DESCRIPTION OF THE SEVERAL VIEWS OF THE DRAWING

These as well as other features of the present invention will become more apparent upon reference to the drawings wherein.

DETAILED DESCRIPTION OF THE INVENTION

Figures 1, 2:
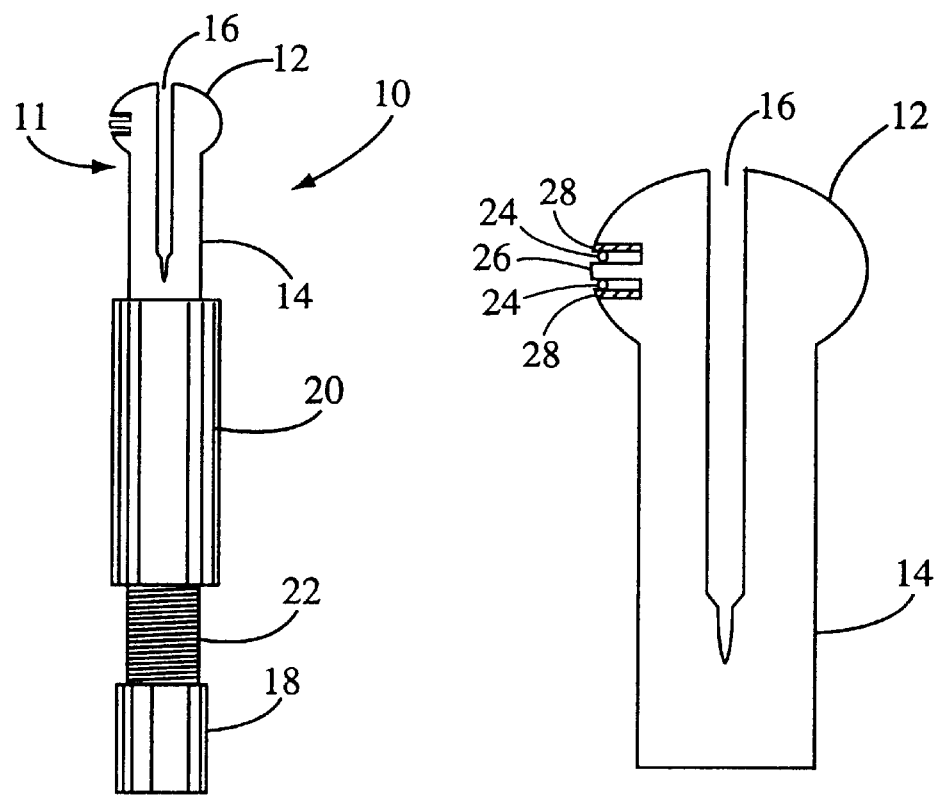
FIG. 1 is a partial cross-sectional view of the probe constructed in accordance with the preferred embodiment of the present invention.
FIG. 2 is an enlarged cross-sectional view of a probe tip for the probe shown in FIG. 1.

Referring now to the drawings wherein the showings are for purposes of illustrating a preferred embodiment of the present invention only, and not for purposes of limiting the same, FIG. 1 illustrates an eddy current probe 10 used for the detection of defects and flaws in structures. The probe 10 is fabricated from a metallic material and comprises a sensing end 11 that has a generally spherical distal tip 12 transitioning into a cylindrical shaft portion 14. In this respect, the spherical distal tip 12 is attached to the cylindrical shaft portion 14. In the preferred embodiment of the present invention, the spherical distal tip 12 may be oblong as shown. However, it will be recognized that other configurations are also possible. A gap or slit 16 is formed within the distal tip 12 of the probe 10, as seen in FIG. 1. Specifically, the slit 16 is disposed within the spherical distal tip 12 and the shaft portion 14 such that the slit 16 bisects the sensing end 11 of the probe 10 into two halves.

As seen in FIG. 1, the shaft portion 14 of the sensing end 11 of the probe 10 is attached to an adjustment shaft 18. Disposed over the adjustment shaft 18 is a probe diameter adjustment sleeve 20 that is slidably moveable over the adjustment shaft 18 and the shaft portion 14 of the sensing end 11. Specifically, the adjustment sleeve 20 is a cylindrical sleeve with an inner diameter slightly larger than the diameter of the shaft portion 14 and the adjustment shaft 18. The adjustment shaft 18 includes a series of threads 22 disposed on an exterior surface thereof. Correspondingly, the adjustment sleeve 20 includes a series of threads (not shown) that engage the threads 22 of the adjustment sleeve 20. In this respect, the adjustment sleeve 20 is movable along the adjustment shaft 18 by rotating the adjustment sleeve 20. The adjustment sleeve 20 can be positioned over the shaft portion 14 of the sensing end 11 in order to constrict the size of the slit 16. The adjustment sleeve 20 will prevent the width of the slit 16 from expanding by contacting the interior surfaces of the adjustment sleeve 20. In this respect, the adjustment sleeve 20 is capable of reducing the diameter of the distal tip 12 by extending the sleeve 20 over the shaft portion 14.

Referring to FIG. 2, the eddy current probe 10 constructed in accordance with the present invention further includes a coil 24 disposed within the spherical distal tip 12. The coil 24 is a conducting wire wound around a core segment 26 of the spherical distal tip 12. The core segment 26 is a cylindrical segment formed by removing a portion of the distal tip 12. The coil 24 is singularly wound around the core segment 26 such that the coil 24 formed thereby is an absolute type coil. As will be recognized, the coil 24 may consist of a single winding or multiple windings depending upon the application. As seen in FIG. 2, the coil 24 and hence core segment 26 is disposed at the apex of the spherical distal tip 12. The coil 24 is in spaced parallel relation to the central axis of the distal tip 12. It will be recognized by those of ordinary skill in the art, that the core segment 26 does not need to by cylindrical, but may be rectangular or triangular and the coil 24 wound thereabout in a corresponding configuration.

In accordance with the present invention, the sensing end 11 further includes a metallic shield 28 disposed about the coil 24. The shield 28 is disposed adjacent to the coil 24 and the interior of the distal tip 12. Accordingly, the shield 28 completely surrounds the core segment 26 and coil 24. The shield 28 is fabricated from a Mu metallic material that focuses and constricts the eddy current field therefrom and enhances detection of a defect profile aspect ratio, as will be further explained below. The Mu shielding is a ferromagnetic material that directs the eddy current field during scanning and determination of defect sizes.

Figure 3:
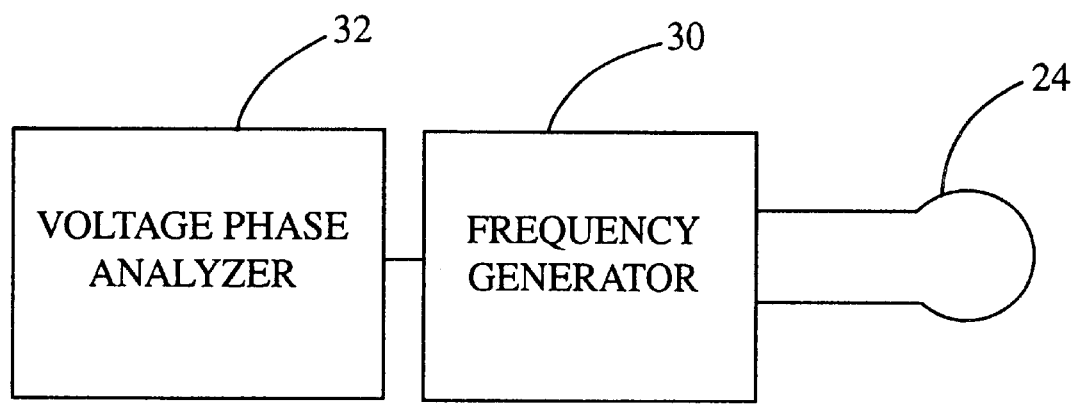
FIG. 3 is a block level diagram showing the analyzing circuitry of the present invention.

In order to detect defects within structures, the coil 24 is in electrical communication with a frequency generator 30 as seen in FIG. 3. The frequency generator 30 is operative to generate a high and low frequency signal within the coil 24. The high frequency signal is approximately 1 MHz and the low frequency signal is approximately 150 KHz. Both of the signals are generated within the coil 24 simultaneously and analyzed separately, as will be further explained below.

In accordance with a preferred embodiment of the present invention, there is provided a method of analyzing defect sizes with the eddy current probe 10 of the present invention. Specifically, the sensing end 11 of the probe 10 is inserted into the hollow interior of a fastener hole. Next, the high and low frequency signals are transmitted simultaneously through the coil 24 through conventional eddy current generation techniques with frequency generator 30. The high and low frequencies are not multiplexed and the coil 24 is operated at both the high and low frequencies simultaneously. As previously mentioned, in the preferred embodiment of the present invention, the low frequency signal is about 150 KHz and the high frequency signal is about 1 MHz. However, it will be recognized, that other frequencies may be applied to the coil 24 simultaneously.

The coil 24 generates an eddy current field within the structure of the fastener hole of the part. The eddy current field is narrowly focused by the Mu shield 28 of the present invention such that the field is directed toward a centralized location of the fastener hole. In this respect, the Mu shield 28 directs the eddy current field to a narrow location within the fastener hole such that the defect may be analyzed with greater precision. The defect is determined from the voltage response and the phase angle characteristics of the two signals applied to the coil 24. In this regard, a voltage and phase analyzer 32 may be connected in electrical communication with the coil 24 as seen in FIG. 3. If a defect is present within the fastener hole, the voltage response and phase angle characteristics of the signals applied to the coil 24 will vary from a prescribed value. By analyzing the variance in both the high and low frequency signals individually, a determination of the crack depth and length can be made. The low frequency signal facilitates a greater penetration depth of the eddy current field within the structure. Therefore the depth of the defect may be found more quickly. On the other hand, the high frequency signal provides a more sensitive resolution as to the size or length of the defect. Accordingly, the high frequency signal can be used for a more precise measurement of the defect's length. By finding the crack depth and length, the aspect ratio of the crack can be determined for analysis. The probe 10 is rotated within the structure in order to fully analyze the interior surface thereof. Therefore, the coil 24 is directed around the interior surface of the structure in order to fully scan the inside thereof.

Tests with the probe 10 constructed in accordance with the present invention show a 50% sensitivity increase in crack size measurement at 1 MHz and a 70% increase in crack size measurement at 150 KHz over the prior art. Accordingly, cracks with a size of 0.020" can be measured reliably with the eddy current probe 10 in order to enhance engineering and inspection efforts of fastener holes. The opportunity to enhance sensitivity at one frequency and evaluate crack size with a frequency-depth penetration analysis is enhanced by simultaneously using two frequencies.

Additional modifications and improvements of the present invention may also be apparent to those of ordinary skill in the art such as applying three or more frequencies to coil 24. Thus, the particular combination of parts described and illustrated herein is intended to represent only a certain embodiment of the present invention, and is not intended to serve as limitations of alternative devices within the spirit and scope of the invention.

What is claimed is:

1. An eddy current probe adapted to detect defects within a plurality of differently sized fastener holes, the probe comprising:

a sensing end operative to generate an eddy current field within the plurality of differently sized fastener holes, the sensing end forming a slit therein;

an adjustment shaft engaged to the sensing end; and an adjustment sleeve movably engaged to the adjustment shaft and extendable to the sensing end, the adjustment sleeve being configured to adjust the sensing end when extended thereto via constriction of the slit formed therein so as to correspond the sensing end to the plurality of differently sized fastener holes.

2. The probe of claim 1 wherein the sensing end comprises a distal tip, the slit being formed through the distal tip to divide the distal tip into two parts.

3. The probe of claim 2 wherein the sensing end comprises a shaft portion engaged between the distal tip and the adjustment shaft, the slit substantially extending through the shaft portion, the adjustment sleeve being extendable to the shaft portion.

4. The probe of claim 2 wherein one of the two parts of the distal tip comprises a coil therein, the coil being operative to generate the eddy current field.

5. The probe of claim 4 wherein the coil comprises a metallic shield disposed therearound, the metallic shield being operative to focus the eddy current field.

6. The probe of claim 5 wherein the metallic shield is fabricated from a Mu metallic material.

7. The probe of claim 4 wherein the sensing end comprises a frequency generator, the frequency generator being operative to generate a high frequency signal and a low frequency signal to the coil to produce the eddy current field thereby.

8. The probe of claim 7 further comprising a voltage and phase angle analyzer in communication with the coil and operative to determine the voltage and phase angle for each of the high and low frequency signals.

9. The probe of claim 1 wherein the adjustment sleeve circumscribes the adjustment shaft to be threadably engaged thereto.

* * * * *